United States Patent
Che et al.

(10) Patent No.: US 7,105,660 B2
(45) Date of Patent: Sep. 12, 2006

(54) INTRAMOLECULAR AMIDATION OF SULFAMATES CATALYZED BY METALLOPORPHYRINS

(75) Inventors: Chi-Ming Che, Hong Kong (HK); Jiang-Lin Liang, Newark, DE (US)

(73) Assignee: University of Hong Kong, Hong Kong (HK)

( * ) Notice: Subject to any disclaimer, the term of this patent is extended or adjusted under 35 U.S.C. 154(b) by 260 days.

(21) Appl. No.: 10/790,810

(22) Filed: Mar. 3, 2004

(65) Prior Publication Data
US 2004/0236099 A1    Nov. 25, 2004

Related U.S. Application Data

(63) Continuation-in-part of application No. 10/202,581, filed on Jul. 23, 2002, now abandoned.

(51) Int. Cl.
*C07D 291/00* (2006.01)
*C07D 419/00* (2006.01)
*C07D 515/00* (2006.01)

(52) U.S. Cl. .......................................... 544/2; 548/122

(58) Field of Classification Search ...................... None
See application file for complete search history.

(56) References Cited

OTHER PUBLICATIONS

Espino et al, "Synthesis of 1,3-Difunctionalized Amine Derivatives through Selective C—H Bond Oxidation" Journal of the American Chemical Society, vol. 123, pp. 6935-6936 (2001).*

Aoyama et al, "Catalytic Reactions of Metalloporphyrins. 3. Catalytic Modification of Hydroboration-Oxidation of Olefin with Rhodium(III) Porphyrin as Catalyst" Journal of Organic Chemistry, vol. 52, pp. 2555-2559 (1987).*

* cited by examiner

*Primary Examiner*—Zachary C. Tucker
(74) *Attorney, Agent, or Firm*—Dickstein, Shapiro, LLP.

(57) ABSTRACT

An intramolecular amidation processes for substrates such as sulfamates using chiral and non-chiral metalloporphyrin complexes which can maximize catalytic activity, enhance efficiency, stereoselectivity and speed of amidation reactions is described. The chiral metalloporphyrin catalyzed amidation of sulfamates exhibits excellent cis-selectivity, affording cyclic sulfamidates with high enantiomeric excess values.

16 Claims, 7 Drawing Sheets

L-786,392 3

Brinzolamide 4

Intramolecular amidation catalyzed by [Ru$^{II}$(TPFPP)(CO)] (1)$^a$

| Entry | Substrates | Products | Yield (%) |
|---|---|---|---|
| 1 |  5 |  11 | 77 |
| 2 |  6 |  12 | 76 |
| 3 |  7 |  (cis)-13 | 88 |
| 4 |  8 |  (cis)-14 | 61 |
| 5 |  9 |  15 | 56 |
| 6 |  10 |  16 | 88 |

$^a$Reaction conditions: catalyst: substrate: PhI(OAc)$_2$ = 0.015: 1: 2; CH$_2$Cl$_2$, 40°C, 2 h.

High turnover intramolecular amidation catalyzed by [Ru$^{II}$(TPFPP)(CO)] (1)

| Entry | Substrate | Product | Yield (%) | Turnover |
|---|---|---|---|---|
| 1[a] | <br>5 | <br>11 | 29 | 290 |
| 2[b] | <br>7 | <br>(cis)-13 | 38 | 301 |

[a]Reaction conditions: catalyst: substrate: PhI(OAc)$_2$ = 1: 1000: 2000; CH$_2$Cl$_2$, 40°C, 20 h.
[b]Reaction conditions: catalyst: substrate: PhI(OAc)$_2$ = 1: 800: 1600; CH$_2$Cl$_2$, 40°C, 20 h.

Asymmetric intramolecular amidation catalyzed by [Ru^II(D_4-Por*)(CO)][a]

| Entry | Substrate | Product | Solvent | Yield (%) | Ee (%)[b] |
|---|---|---|---|---|---|
| 1 |  5 |  11 | CH₂Cl₂ | 77 | 46 |
| 2 | | | C₆H₆ | 63 | 79 |
| 3 | | | C₆H₆ | 48 | 84[c] |
| 4 |  8 |  14 | CH₂Cl₂ | 57 | 71 |
| 5 | | | C₆H₆ | 53 | 81 |
| 6 | | | C₆H₆ | 39 | 82[c] |
| 7 | | | PhMe | 39 | 77[d] |
| 8 |  9 |  15 | CH₂Cl₂ | 53 | 69 |
| 9 | | | C₆H₆ | 43 | 82 |
| 10 | | | C₆H₆ | 35 | 87[c] |

[a]Reaction conditions: catalyst: substrate: PhI(OAc)₂ = 1: 10: 14; 40°C for 2 h. [b]Ee was determined by HPLC using chiral OD column. [c]Reaction at 4°C and 8 h. [d]Reaction at 0°C and 8 h.

(1S,2R)-14        17

18

US 7,105,660 B2

INTRAMOLECULAR AMIDATION OF SULFAMATES CATALYZED BY METALLOPORPHYRINS

This is a continuation-in-part of application Ser. No. 10/202,581, filed Jul. 23, 2002 now abandoned.

FIELD OF THE INVENTION

The invention relates to methods for direct intramolecular amidation of sulfamates affording cyclic sulfamidates. The method represents an example of asymmetric intramolecular amidation of sulfamate esters with high ee (enantiomeric excess) values, (typically 46–87% ee).

BACKGROUND OF THE INVENTION

Cyclic sulfamidates and sulfonamides are useful building blocks for organic synthesis and drug discovery. Major recent pharmaceutical applications include the carbapenem antibiotic L-786,392 3 and brinzolamide 4 for the treatment of glaucoma (Rosen et al. *Science* (1999), 283, 703; Dauban et al. *Org. Lett.* (2000), 2, 2327; Dauban et al. *Tetrahedron Lett.* (2001), 42, 1037; FIG. 2). Cyclic sulfamidates have also been utilized in the preparation of amino acids (Baldwin et al. *Tetrahedron: Asymmetry* (1990), 1, 881; Boulton et al. *J. Chem. Soc., Perkin Trans.* 1 (1999), 1421; Halcomb et al. *J. Am. Chem. Soc.* (2002), 124, 2534) and have been shown to serve as useful chiral auxiliaries for organic synthesis (Oppolzer et al. *Tetrahedron Lett.* (1994), 35, 3509; Ahn et al. *Tetrahedron Lett.* (1998), 39, 6321; Lin et al. *Tetrahedron* (1999), 55, 13983).

Pioneering work by Breslow and co-workers in 1983 demonstrated catalytic intramolecular amidation of sulfonamides with either transition metal porphyrin complexes or rhodium acetate as catalysts gave cyclic sulfonamides in good yields (Breslow et al. *J. Am. Chem. Soc.* (1983), 105, 6728). Recent studies by Du Bois and co-workers reported rhodium acetate to be an efficient catalyst for intramolecular amidation of sulfamate esters, affording the corresponding cyclic sulfamidates in good to high yields (Du Bois et al. *J. Am. Chem. Soc.* (2001), 123, 6935). However, the challenge still remains to seek more stereoselective catalysts for the synthesis of optically active cyclic sulfamidates. To our knowledge, the asymmetric intramolecular amidation of such substrates using chiral catalysts is not known.

Metalloporphyrin catalyzed intermolecular nitrogen-atom transfer has attracted considerable attention because of their unique relationship to heme-containing enzymes, high stereoselectivity and catalytic turnover (Che et al. *Org. Lett.* (2000), 2, 2233). Moderate ee values have been obtained for asymmetric aziridination of alkenes and amidation of saturated C—H bonds (Che et al. *Chem. Commun.* (1997), 2373; Che et al. *Chem. Commun.* (1999), 2377; Marchon et al. *Chem. Commun.* (1999), 989; Che et al. *Chem. Eur. J.* (2002), 1563). The successful isolation of bis(tosylimido)ruthenium(VI) porphyrins have provided useful insights into the mechanism of ruthenium porphyrin catalyzed intramolecular nitrogen-atom transfer reactions (Che et al. *J. Am. Chem. Soc.* (1999), 121, 9120; Che et al. *Chem. Eur. J.* (2002), 1563).

The present invention describes the first intramolecular amidation of sulfamates catalyzed by a metalloporphyrin and asymmetric intramolecular amidation of sulfamidates catalyzed by a transition metal complex supported by a porphyrin macrocycle. The target cyclic sulfamidates can be easily converted to α- or β-amino alcohols (Du Bois et al. *J. Am. Chem. Soc.* (2001), 123, 6935), which are important precursors for drug synthesis and for the synthesis of chiral ligands for asymmetric catalysis (Kajiro et al. *Synlett* (1998), 51; Davies et al. *Tetrahedron Lett.* (1996), 37, 813; Ghosh et al. *J. Am. Chem. Soc.* (1996), 118, 2527).

DETAILED DESCRIPTION OF THE INVENTION

The present invention provides an intramolecular amidation process using a non-chiral metalloporphyrin catalyst and a chiral metalloporphyrin catalyst represented by structural formula:

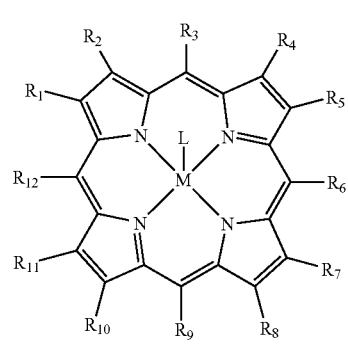

1 wherein each $R_1$–$R_{12}$ is independently H, optionally substituted hydroxyl, optionally substituted amino, halogen, —CN, —$NO_2$, optionally substituted $C_{1-20}$ alkyl, optionally substituted phenyl; optionally substituted naphthyl; optionally substituted anthracenyl, —SR$^{13}$, —SO$_2$R$^{13}$, —CO$_2$R$^{13}$, and optionally substituted heteroatom-containing aromatic ring, in which the optional substituents are independently selected from the foregoing alkyl, phenyl, naphthyl, anthracenyl and heteroatom-containing aromatic groups; R$^{13}$ is independently selected from the same groups as R$^1$ other than —SR$^{13}$ and —SO$_2$R$^{13}$; and L is CO or R$^1$. The various R groups may be optically pure or can be stereo- and regioisomers.

Figure 1:
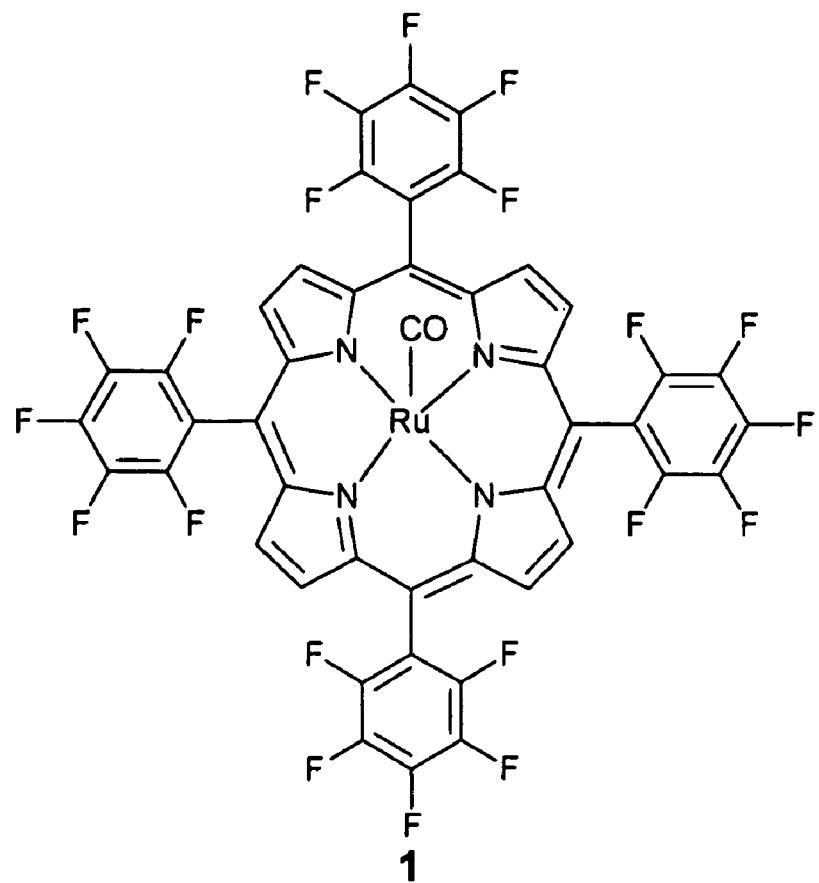
FIG. 1 provides representative examples of metalloporphyrin catalysts capable of catalyzing intramolecular amidation of sulfamates with high efficiency and high diastereo- and enantio-selectivity.
Figure 1:
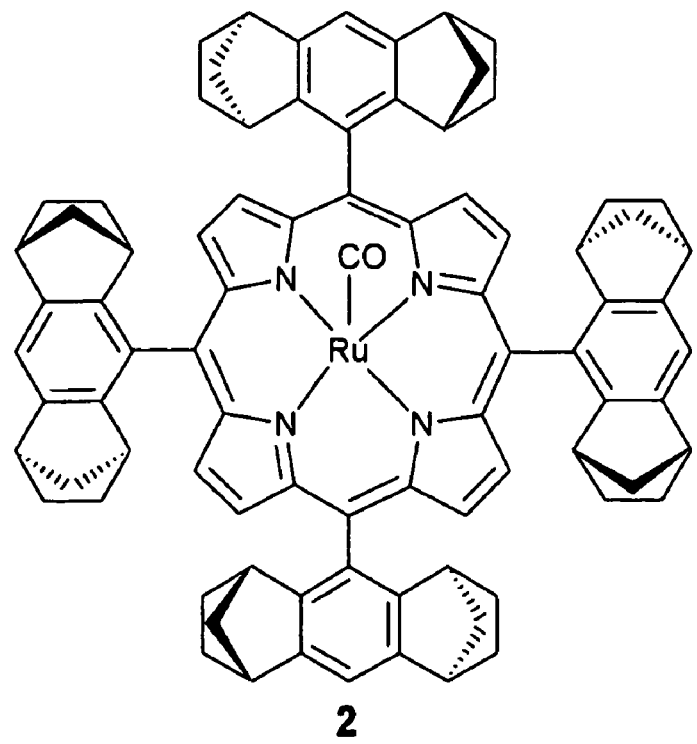
Figure 2:
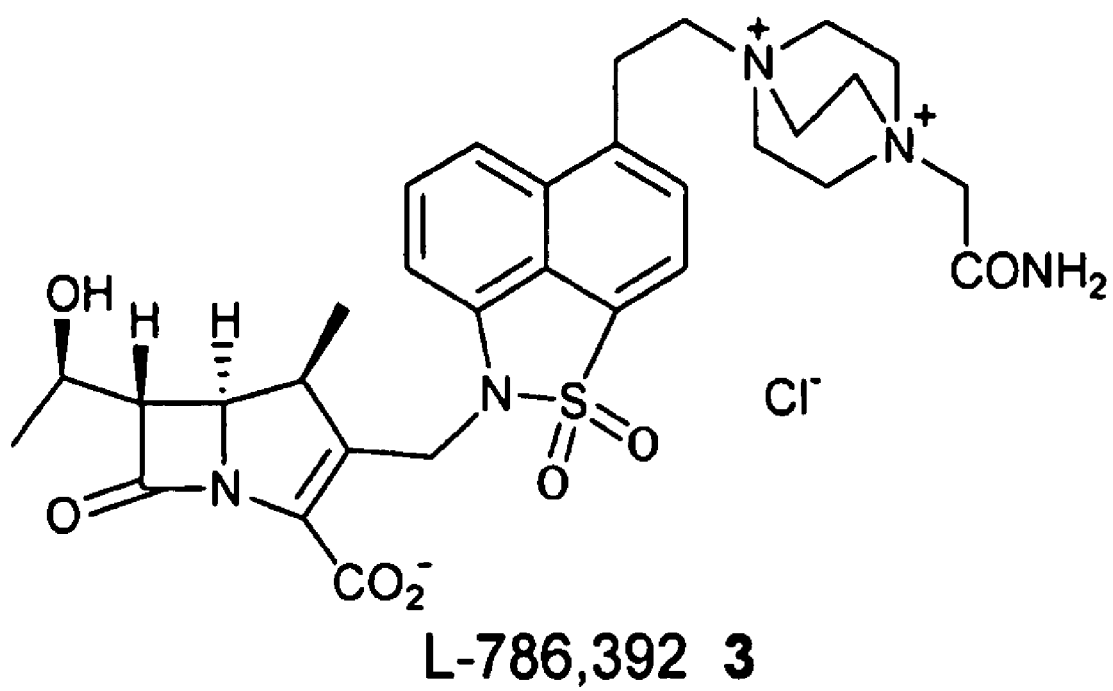
FIG. 2 provides representative examples of drugs containing the cyclic sulfonamide unit.
Figure 2:
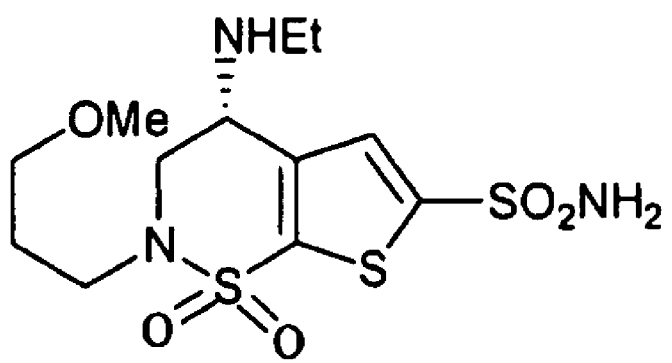
Figure 3:
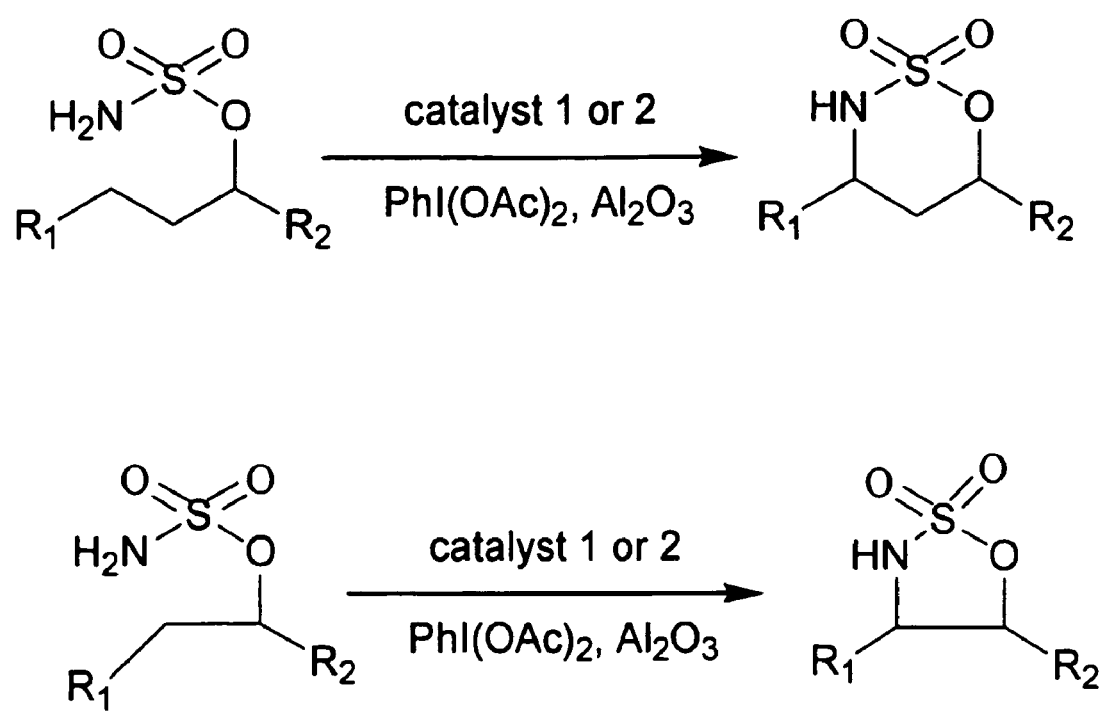
FIG. 3 illustrates the described method which involves the direct intramolecular amidation of sulfamates using metalloporphyrins as general and efficient catalysts.

In an embodiment of this invention, the metalloporphyrin is a transition metal porphyrin, such as ruthenium, manganese, iron, osmium, copper or cobalt porphyrin. In an embodiment of this invention, the porphyrin ligand is a tetraphenylporphyrin and the phenyl rings are attached at the meso-positions of the porphyrin. In an embodiment of the present invention, the catalysts are capable of exhibiting both regio- and stereo-selectivity. Two of the preferred catalysts are shown in FIG. 1. In an embodiment of the present invention, the catalyst is capable of selectively catalyzing intramolecular amidation of saturated C—H bonds. In an embodiment of the present invention, the catalyst is capable of catalyzing asymmetric intramolecular amidation of saturated C—H bonds. In an embodiment of this invention, the stereoselectivity is the formation of only cis-configuration cyclic sulfamidates.

Additionally, the present invention provides a method for the preparation of cyclic sulfamidates with the catalysts from sulfamates as starting materials. Further, the present invention provides a method for producing cis-cyclic sulfamidates with the catalyst. The present invention also provides a method for producing optically active cyclic sulfamidates with the catalyst. Preferably, the method involves the use of an oxidant which selectively alters the oxidation state of the substrate, preferably in the presence of a solvent and preferably in the the presence of a base. The solvent can be MeOH, MeCN, DMF, C$_4$H$_4$Cl$_2$, CH$_2$Cl$_2$, and benzene. Typical oxidants include PhI(OAc)$_2$, PhIO and NBS (N-bromosuccinimide). Bases, which scavenge by-products, include Al$_2$O$_3$, MgO, ZnO, K$_2$CO$_3$ and NaOH. In an embodiment of this invention, the substrate is a sulfamate, a sulfamate derivative, or a hydrocarbon containing a sulfonylamide functional group. As shown in the figures, carbon to which the sulfonylamide moiety is attached can be a part of a cyclic or non-cyclic moiety, which in turn can be substituted with a functional group such as —CO$_2$Me or by an aromatic or cycloaliphatic group.

As used herein, the term, "stereoselective" refers to selection of an optical isomer. "Enantioselectivity" represents the maximal asymmetric induction and minimal racemization of the optically active products. The term "turnover" refers to the relative number of molecules of products per number of molecules of catalyst prior to the exhaustion of a given reaction.

EXAMPLES

Example 1

Intramolecular Amidation of Sulfamate Esters Catalyzed by Electron-Deficient Ruthenium Porphyrin 1

The invention relates to a direct method for the synthesis of cyclic sulfamidates using ruthenium porphyrin 1 (prepared according to: Murahashi et al. *Tetrahedron Left.* (1995), 36, 8059; Groves et al. *J. Am. Chem. Soc.* (1996), 118, 8961) as a general and effective catalyst for the direct intramolecular amidation of sulfamates.

Typical conditions employ 1.5 mol % of 1, 1 equiv. of sulfamate ester, 2 equiv. of PhI(OAc)$_2$, 2.5 equiv. of anhydrous Al$_2$O$_3$ (pH=7–7.4) in CH$_2$Cl$_2$ (distilled from CaH$_2$ prior to use) under argon at 40° C. for 2 h. Commercially available Al$_2$O$_3$ was dried to a constant weight at 250° C. for 12 h. The reaction mixture was cooled to 25° C., diluted with 5 mL of CH$_2$Cl$_2$, and filtered through a pad of Celite®. The filter cake was rinsed with 2×5 mL of CH$_2$Cl$_2$ and the combined filtrates were evaporated under reduced pressure. The residue was purified by silica gel chromatography (Merck, 230–400 mesh) to afford the corresponding cyclic sulfamidates. AcOH generated as a by-product from PhI (OAc)$_2$ was scavenged from the reaction mixture by addition of base. Following a series of control experiments, Al$_2$O$_3$ proved to be the best among MgO, ZnO, K$_2$CO$_3$, Al$_2$O$_3$ and NaOH, in that it gave the highest product yields.

Figure 4:
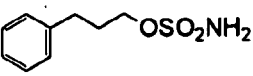
FIG. 4 provides representative examples of intramolecular amidation of sulfamates catalyzed by an electron-deficient ruthenium porphyrin to give the corresponding cyclic sulfamidates in good to excellent yields and excellent diastereoselectivity.
Figure 4:
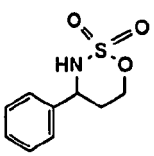
Figure 4:
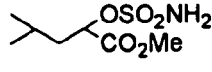
Figure 4:
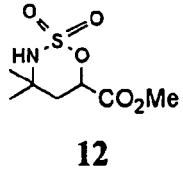
Figure 4:
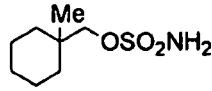
Figure 4:
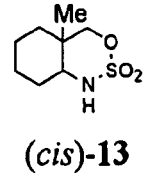
Figure 4:
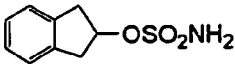
Figure 4:
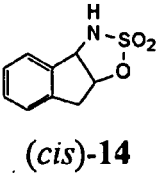
Figure 4:
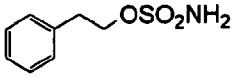
Figure 4:
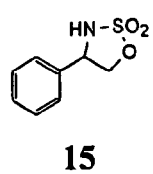
Figure 4:
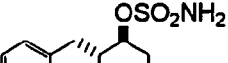
Figure 4:
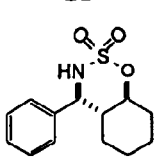

With only 1.5 mol % catalyst loading, sulfamates 5–10 were converted to the corresponding cyclic sulfamidates 11–16 in good to high yields (see FIG. 4). The highest yield (88%) was achieved for the intramolecular amidations of 7 and 10. Catalyst 1 shows high catalytic efficiency and excellent cis-selectivity. For substrates 7, 8 and 10, only cis-cyclic sulfamidates 12, 13 and 16 were obtained, respectively. The trans-cyclic sulfamidates were undetected. This shows that ruthenium porphyrin 1 has better stereoselectivity than rhodium acetate (a 8:1 mixture of cis and trans isomers was obtained for the reaction of 8 catalyzed by rhodium acetate. See: Du Bois et al. *J. Am. Chem. Soc.* (2001), 123, 6935). The oxidant used in the catalytic reaction is PhI(OAc)$_2$, which is commercially available. For substrates 5–7, and 10, six- rather than five-membered ring heterocycles 11–13 and 16 were formed in high yields (76–88%). For substrates 8 and 9, five-membered ring formation gave cycloadducts 14 and 15 in moderate yields of 61 and 56%, respectively.

All the target cyclic sulfamidates were characterized by $^1$H, $^{13}$C and NOESY NMR spectroscopy and HRMS spectrometry. The spectral data of 11–14 are identical with those reported in the literature (see: Du Bois et al. *J. Am. Chem. Soc.* (2001), 123, 6935). 9: $^1$H NMR (CDCl$_3$, 400 MHz): δ=7.29 (m, 5H), 4.82 (s, 2H), 4.37 (t, J=9.3 Hz, 2H), 3.03 (t, J=9.2 Hz, 2H); $^{13}$C NMR (CDCl$_3$, 100 MHz): δ=136.4, 128.9, 128.7, 127.0, 71.4, 35.2; HRMS (EI) calcd. for C$_8$H$_{11}$NO$_3$S: 201.0460. found: 201.0456. 10: $^1$H NMR (CDCl$_3$, 400 MHz) 7.23 (m, 5H), 4.66 (s, 2H), 4.34 (m, 1H), 3.15 (dd, 1H, J=13.6 Hz), 2.32 (m, 2H), 1.10–1.86 (m, 8H); $^{13}$C NMR (CDCl$_3$, 100 MHz) 140.0, 129.2, 128.3, 126.0, 87.2, 44.0, 38.9, 32.4, 30.0, 24.5, 24.4; HRMS (EI) calcd. for C$_{13}$H$_{19}$NO$_3$S: 269.1087. found: 269.1090. 15: $^1$H NMR (CDCl$_3$, 400 MHz), 7.43 (m, 5H), 5.07 (m, 1H), 4.84 (m, 2H), 4.45 (t, J=6.5 Hz, 1H); $^{13}$C NMR (CDCl$_3$, 100 MHz) 135.3, 129.5, 129.4, 126.7, 75.0, 59.6; HRMS (EI) calcd. for C$_8$H$_9$NSO$_3$: 199.0303. found: 199.0297. 16: $^1$H NMR (CDCl$_3$, 400 MHz) 7.37 (m, 5H), 4.60 (m, 1H), 4.39 (m, 2H), 2.14 (m, 1H), 1.10–1.85 (m, 8H); $^{13}$C NMR (CDCl$_3$, 100 MHz) 136.7, 129.3, 129.1, 127.3, 86.9, 64.3, 45.3, 31.8, 29.7, 24.8, 24.4; HRMS (EI) calcd. for $C_{13}H_{17}NO_3S$: 267.0929. found: 267.0935.

Example 2

Figure 5:
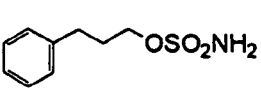
FIG. 5 provides representative examples of intramolecular amidation of sulfamates catalyzed by an electron-deficient ruthenium porphyrin with high turnover numbers.
Figure 5:
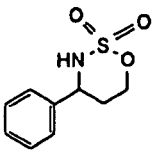
Figure 5:
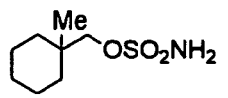
Figure 5:
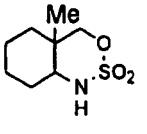

Turnover number refers to the relative number of molecules of product per number of molecules of catalyst prior to the exhaustion of a given reaction and shows a very important aspect of catalyst efficiency. The turnover numbers for the analogous rhodium acetate catalyzed reactions do not exceed 50 (see: Du Bois et al. *J. Am. Chem. Soc.* (2001), 123, 6935). With electron-deficient ruthenium porphyrin 1 as catalyst, intramolecular amidation of 5 and 7 afforded turnover numbers of 290 and 301, respectively (FIG. 5). This shows that 1 is more robust catalyst than rhodium (II,II) dimmer complexes (the reaction conditions are almost the same as those for EXAMPLE 1, and with a lower catalyst loading in EXAMPLE 2. See FIG. 5 footnote).

Example 3

Asymmetric Intramolecular Amidation of Sulfamate Ester Catalyzed by Chiral Ruthenium Porphyrin 2

Figure 6:
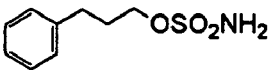
FIG. 6 provides representative examples of asymmetric intramolecular amidation of sulfamates catalyzed by a chiral ruthenium porphyrin with high enantioselectivity.
Figure 6:
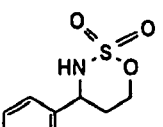
Figure 6:
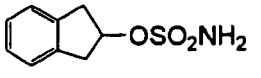
Figure 6:
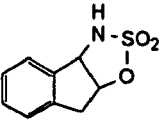
Figure 6:
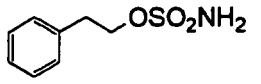
Figure 6:
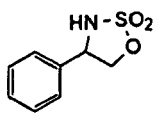

With chiral ruthenium porphyrin 2 as catalyst (prepared according to: Che et al. *Chem. Commun.* (1997), 1205), sulfamates 5, 8 and 9 undergo enantioselective C—H insertion to give the corresponding cyclic sulfamidates with high ee values (typically 46–87%, FIG. 6). As shown in FIG. 6, an ee (enantiomeric excess) of 46% or more can be achieved. In order to reduce the amount of by-products, the substrate to PhI(OAc)$_2$ ratio was decreased from 2 to 1.4. Solvent has a very important effect on ee values obtained. For example, reaction of sulfamate ester 5 in CH$_2$Cl$_2$ gave 11 with 46% ee (entry 1). In comparison, the analogous reaction carried in C$_6$H$_6$ gave 11 with an ee value of 79% (entry 2). Similar outcomes were obtained for substrates 8 and 9.

Similarly, reaction temperature has an effect on the ee values. With benzene as solvent, lowering the reaction temperature to 4° C. resulted in an increase in ee values (entries 2 and 3: from 79 to 84%; entries 5 and 6: from 82 to 87%; entries 8 and 9: from 81 to 82%).

Figure 7:
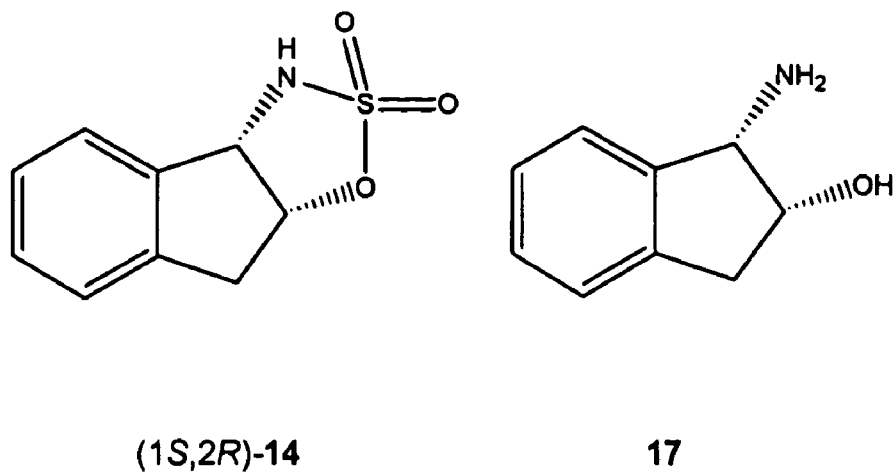
FIG. 7 provides representative examples of pharmaceutical applications of α-amino alcohols.
Figure 7:
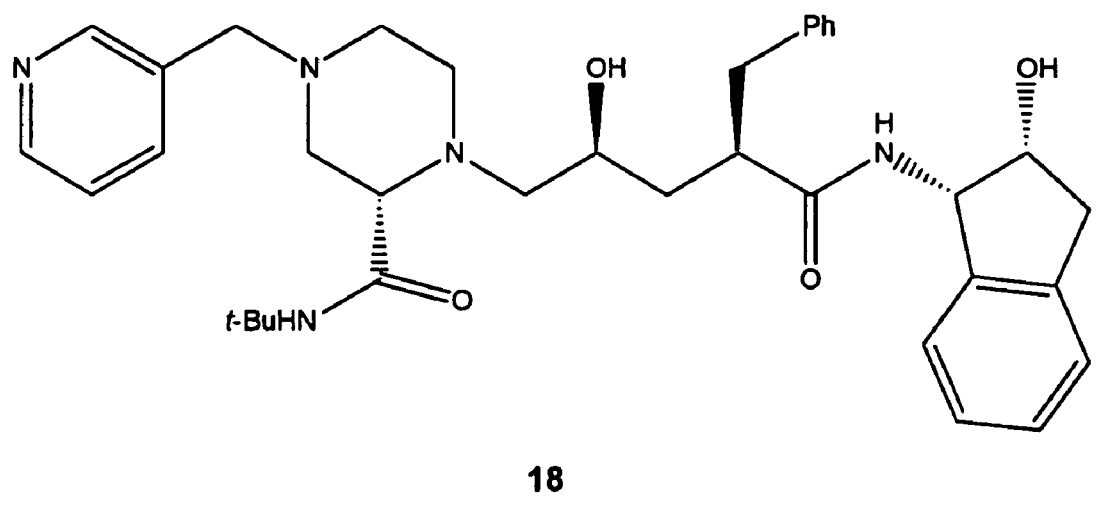

The present invention provides an efficient method for the synthesis of chiral cyclic sulfamidates. These compounds are useful synthetic intermediates in the preparation of optically active α- or β-amino alcohols of biological importance. For example, optically active 17 is currently receiving considerable attention as a key component of the HIV protease inhibitor Indinavir 18 (see: Hiyama et al. *Synlett* (1998), 51. FIG. 7). Amino alcohol 17 can be prepared from (1S,2R)-14 upon hydrolysis (see: Du Bois et al. *J. Am. Chem. Soc.* (2001), 123, 6935). Using commercially available achiral 2-indanol, amino alcohol 17 can be obtained in 3 steps; optically active 17 requires 8 steps from the chiral amino acid (see: Hiyama et al. *Synlett* (1998), 51).

What is claimed is:

1. A method for synthesizing a cyclic sulfamidate from a sulfamate compound comprising a sulfonylamide functional group comprising the step of catalyzing the reaction of an oxidant with said sulfamate compound with a catalytic amount of metalloporphyrin as catalyst for producing the cyclic sulfamidate.

2. The method according to claim 1, wherein said sulfamate compound is a sulfamate ester.

3. The method according to claim 1, wherein the oxidant is selected from the group consisting of PhI(OAc)$_2$, PhIO, and NBS.

4. The method according to claim 1, effected in the presence of an organic solvent selected from the group consisting of acetonitrile, DMF, C$_4$H$_4$Cl$_2$, CH$_2$Cl$_2$, and benzene.

5. The method according to claim 1, effected in the presence of an inorganic base is selected from the group consisting of Al$_2$O$_3$, MgO, ZnO, K$_2$CO$_3$, and NaOH.

6. The method according to claim 1, wherein the metalloporphyrin is a transition metal metalloporphyrin.

7. The method according to claim 6, wherein the transition metal metalloporphyrin is selected from the group consisting of ruthenium, manganese, iron, cobalt, copper and osmium metalloporphyrin.

8. The method according to claim 7, wherein the metalloporphyrin is ruthenium porphyrin.

9. The method of claim 3, wherein the method is effected in the presence of an inorganic base selected from the group consisting of Al$_2$O$_3$, MgO, ZnO, K$_2$CO$_3$, and NaOH; the metalloporphyrin is a transition metal metalloporphyrin; and wherein the method is effected in the presence of an organic solvent selected from the group consisting of acetonitrile, DMF, C$_4$H$_4$Cl$_2$, CH$_2$Cl$_2$ and benzene.

10. The method according to claim 1, wherein the catalyst is represented by the structure:

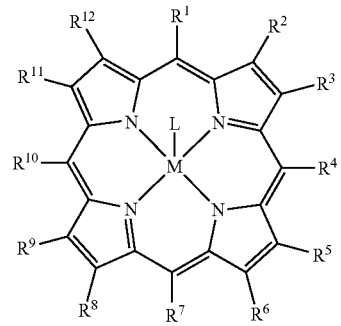

wherein M is a transition metal;

each $R^1$–$R^{12}$ is independently selected from the group consisting of —H, -halogen, —CO$_2$R$^{13}$, —CN, —NO$_2$, SR$^{13}$, SO$_2$R$^{13}$, optionally substituted hydroxyl, optionally substituted amino, halogen, optionally substituted C$_{1-20}$ alkyl, optionally substituted phenyl; optionally substituted naphthyl; optionally substituted anthracenyl, and optionally substituted heteroatom-containing aromatic ring, in which the optional substitutents are independently selected from the foregoing alkyl, phenyl, naphthyl, anthracenyl and heteroatom-containing aromatic groups; $R^{13}$ is independently selected from the same groups as $R^1$ other than —SR$^{13}$ and L is CO or as defined as for $R^1$.

11. The method according to claim 10, wherein the metalloporphyrin catalyst has the structure:

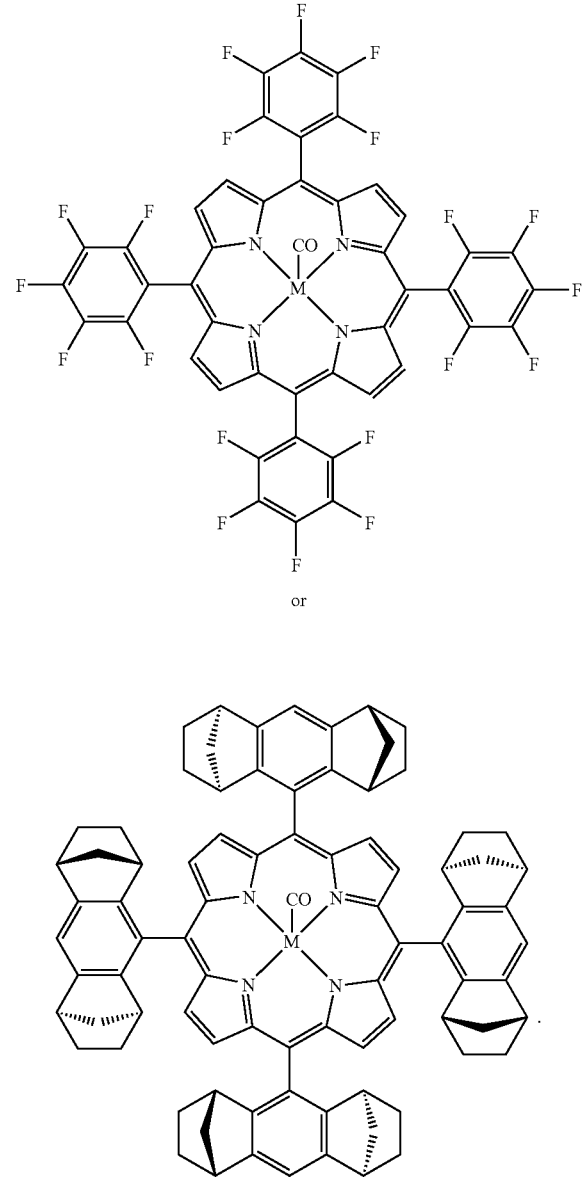

or

12. The method according to claim 11, wherein the catalyst is selected from the group consisting of:

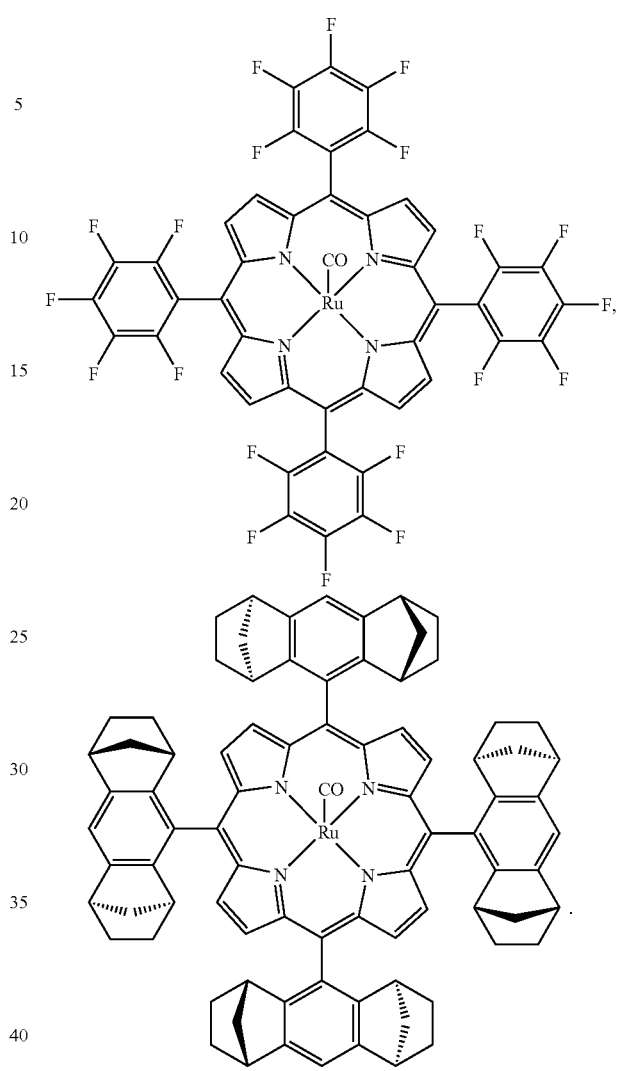

13. The method of claim 9, wherein the catalyst exhibit cis-diastereoselectivity.

14. The method of claim 9, wherein the catalyst exhibits enantioselectivity and yields the corresponding cyclic sulfamidate with an enantomeric excess value of at least 46.

15. The method of claim 9, wherein the catalyst exhibits a product turnover number of at least 290.

16. The method of claim 9, wherein the catalyst exhibits a product turnover number of at least 290.

* * * * *